(12) United States Patent
Lee et al.

(10) Patent No.: US 10,927,073 B2
(45) Date of Patent: Feb. 23, 2021

(54) COMPOUND FOR A CURABLE COMPOSITION

(71) Applicant: LG Chem, Ltd., Seoul (KR)

(72) Inventors: Ji Yeong Lee, Daejeon (KR); Ji Young Hwang, Daejeon (KR); Se Woo Yang, Daejeon (KR)

(73) Assignee: LG Chem, Ltd.

( * ) Notice: Subject to any disclaimer, the term of this patent is extended or adjusted under 35 U.S.C. 154(b) by 219 days.

(21) Appl. No.: 16/074,958

(22) PCT Filed: Mar. 31, 2017

(86) PCT No.: PCT/KR2017/003576
§ 371 (c)(1),
(2) Date: Aug. 2, 2018

(87) PCT Pub. No.: WO2017/171490
PCT Pub. Date: Oct. 5, 2017

(65) Prior Publication Data
US 2019/0031603 A1    Jan. 31, 2019

(30) Foreign Application Priority Data
Mar. 31, 2016 (KR) .................. 10-2016-0039685

(51) Int. Cl.
*C08G 18/48* (2006.01)
*C07C 271/24* (2006.01)
(Continued)

(52) U.S. Cl.
CPC ............ *C07C 271/24* (2013.01); *C08G 18/34* (2013.01); *C08G 18/4812* (2013.01);
(Continued)

(58) Field of Classification Search
CPC .............. C07C 271/24; C08G 18/4812; C08G 18/8108; C08G 18/8116; C08G 18/4825
See application file for complete search history.

(56) References Cited

U.S. PATENT DOCUMENTS 3,856,830 A    12/1974   Kuehn
4,554,336 A    11/1985   Kidd et al.
(Continued)

FOREIGN PATENT DOCUMENTS

CN      104710606 A    6/2015
EP      0168173 A1    1/1986
(Continued)

OTHER PUBLICATIONS

WO-2014/109223_Jul. 2014_English Translation.*
(Continued)

*Primary Examiner* — Michael L Leonard
(74) *Attorney, Agent, or Firm* — Lerner, David, Littenberg, Krumholz & Mentlik, LLP

(57) ABSTRACT

The present application relates to a curable composition, a cured product and uses of the curable composition and the cured product. By comprising the curable compound having a certain structure, the present application can provide a curable composition which can increase cohesiveness of the cured product without increasing viscosity of the composition before curing, also minimize the increase of the elastic modulus, and also minimize the ratio of a nonreactive oligomer with an effect of improving the interfacial adhesion. The curable composition can be applied to a variety of optical applications and can be usefully used, for example, for bonding various optical functional members in a display device, for example, for directly bonding a touch panel and a display panel.

12 Claims, 2 Drawing Sheets

(51) Int. Cl.
*C08G 65/333* (2006.01)
*C08G 18/81* (2006.01)
*C09J 175/16* (2006.01)
*C08G 18/34* (2006.01)

(52) U.S. Cl.
CPC ..... *C08G 18/4825* (2013.01); *C08G 18/4829* (2013.01); *C08G 18/8108* (2013.01); *C08G 18/8116* (2013.01); *C08G 65/33344* (2013.01); *C09J 175/16* (2013.01)

(56) References Cited

U.S. PATENT DOCUMENTS

| | | | | |
|---|---|---|---|---|
| 6,576,451 | B1* | 6/2003 | Sumino | C02F 3/108 435/182 |
| 6,734,249 | B1 | 5/2004 | Bulluck et al. | |
| 2012/0282671 | A1 | 11/2012 | Zhao et al. | |
| 2014/0178619 | A1* | 6/2014 | Niiyama | B32B 37/12 428/40.1 |
| 2015/0241599 | A1 | 8/2015 | Hunt et al. | |

FOREIGN PATENT DOCUMENTS

| | | |
|---|---|---|
| JP | S59059990 A | 4/1984 |
| JP | 2000351818 A | 12/2000 |
| JP | 2001346575 A | 12/2001 |
| JP | 200555641 A | 3/2005 |
| JP | 2013515791 A | 5/2013 |
| TW | 201418290 A | 5/2014 |
| WO | WO-20147/109223 * 7/2014 ............ C08F 299/06 |

OTHER PUBLICATIONS

Arai M, Fujii T, Inoue H, Kuwahara S, Katayama K. Curing Dynamics of Photopolymers Measured by Single-shot Heterodyne Transient Grating Method. Analytical Sciences. Apr. 10, 2013;29(4):401-4. XP55558389A.
Extended European Search Report including Written Opinion for EP17775914.9 dated Feb. 26, 2019.
Search report from International Application No. PCT/KR2017/003576, dated Jul. 21, 2017.
Park, Spencer, et al., "Self-assembled nanoplatform for targeted delivery of chemotherapy agents via affinity-regulated molecular interactions." Biomaterials, vol. 31; Accepted Jun. 23, 2010, Available online Jul. 29, 2010, pp. 7766-7775.
Seto, J., et al., "Electron Beam Curing of Acrylic Oligomers." Radiat. Phys. Chem., vol. 25, Nos. 4-6, 1985, pp. 567-579.
Chemical Abstrct compound, STN express, RN 51667-68-6 (Entered STN: Nov. 16, 1984).
Search report from Office Action dated Oct. 27, 2017 from Taiwan Application No. 106110095.
Search report from Office Action dated Mar. 16, 2018 from Taiwan Application No. 106110095.
Chinese Search Report for Application No. 201780013072.1, dated Mar. 19, 2020, pp. 1-2.

* cited by examiner

[Figure 1]
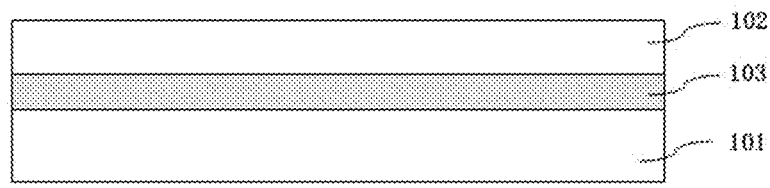
[Figure 2]
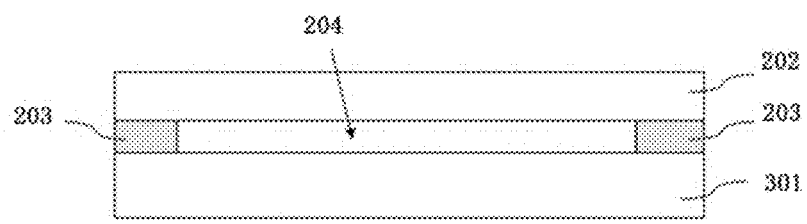
[Figure 3]
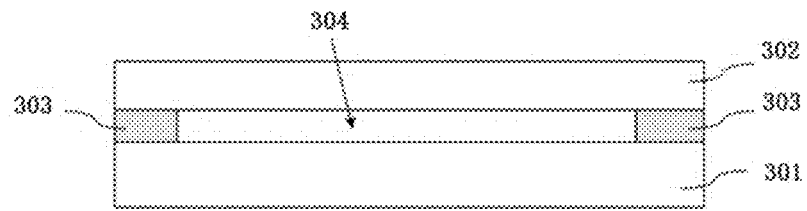

[Figure 4]
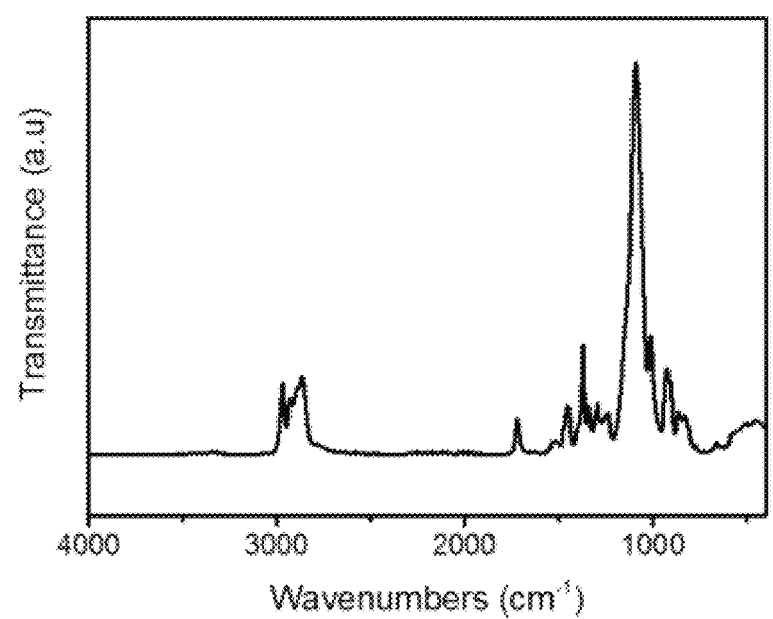

COMPOUND FOR A CURABLE COMPOSITION

CROSS-REFERENCE TO RELATED APPLICATIONS

The present application is a national phase entry under 35 U.S.C. § 371 of International Application No. PCT/KR2017/003576 filed Mar. 31, 2017, which claims priority from Korean Patent Application No. 10-2016-0039685 filed Mar. 31, 2016, all of which are incorporated herein by reference.

TECHNICAL FIELD

The present application relates to a compound, a curable composition and a use thereof.

BACKGROUND ART

A display device may be equipped with, for example, a touch panel (302) mounted on a display panel (301), as shown in FIG. 3. In this case, in order to protect the display panel, an air gap (304) may be formed between the display panel and the touch panel by interposing a spacer (303) between the display panel and the touch panel. However, such an air gap (304) allows to lower contrast through light scattering and also hinders panel thinning.

Patent Document 1 proposes a technique of filling a resin in the air gap. The resin thus filled in the air gap is also referred to as an OCR (Optically Clear Resin). Physical properties required for such an OCR are shrinkage ratio, dielectric constant, degree of cross-linking and adhesive characteristics, and the like, including optical properties.

For example, the OCR requires as low a viscosity as possible before curing for effectively filling the air gap, but after curing, adequate interfacial adhesion and cohesiveness must be ensured. In addition, even when the cured OCR has excessively high elastic modulus, various problems may be caused, so that an appropriate elastic modulus level also needs to be maintained.

PRIOR ART DOCUMENT

Patent Document 1

Patent Document 1: Japanese Laid-Open Patent Publication No. 2005-55641

DISCLOSURE

Technical Problem

The present application provides a compound, a curable composition and a use thereof.

Technical Solution

The present application relates to a compound. The compound may be represented by Formula 1 below. The compound represented by Formula 1 below may be an oligomer compound.

[Formula 1]

In Formula 1, A may be a core comprising a polyalkylene oxide unit, B maybe a chain connected to the core, where the chain comprises a polyalkylene oxide unit and is a chain in which a polymerizable functional group is terminally linked, n may be a number of 1 or more, m may be a number of 1 or more, n+m may be a number of 3 or more, and K may be -L-R.

L in the K is a linker, and R is a polymerizable functional group.

The compound of Formula 1 has a structure in which three or more chains (B and/or K) are linked to the core A. Such a structure can be called a radial structure. Such a structure can contribute to keeping the curable composition at low viscosity. The terminal of the chain (B and/or K) of Formula 1 may be a polymerizable functional group.

A representative example of the polymerizable functional groups as referred to herein is an acryloyl group, an acryloyloxy group, a methacryloyl group, a methacryloyloxy group, and the like, but is not limited to the above, and any type of polymerizable functional group known in the art can be applied.

The compound of Formula 1 is a multifunctional compound containing at least three polymerizable functional groups, and such a compound can be used for forming a curable composition. When the curable composition is cured with appropriate viscosity, the compound of Formula 1 can exhibit excellent cohesiveness and adhesion without increasing the excessive elastic modulus.

The core and chain of the compound of Formula 1 may each contain at least one polyalkylene oxide unit. The chain containing the polyalkylene oxide unit may be a chain represented by K and/or B in Formula 1, for example, a chain represented by B.

In the present application, the term polyalkylene oxide or polyalkylene glycol may refer to an object comprising two or more alkylene oxide units having a linear or branched alkylene group with 2 to 12 carbon atoms. The number of carbon atoms in the alkylene group may be 2 to 8 or 2 to 4, or 2 or 3.

In the present application, a specific example of the polyalkylene oxide includes polyethylene oxide or polypropylene oxide, and a specific example of polyalkylene glycol includes polyethylene glycol and polypropylene glycol.

In one example, the core (A) of Formula 1 may be a core derived from polyalkylene polyol. The term polyalkylene polyol compound herein means a compound having a polyalkylene oxide unit and also containing three or more hydroxy groups. Here, the hydroxy group may be present at the terminal of the polyalkylene polyol compound. For example, the chain (B and/or K) may be added to at least one of the terminal hydroxy groups of the polyalkylene polyol compound to form the compound of Formula 1. The polyalkylene polyol compound forming the core (A) may be a triol or higher alcohol, that is, a compound containing at least three terminal hydroxy groups, and the chain (B and/or K) may be added thereto via such a hydroxy group. The number of terminal hydroxyl groups contained in the polyalkylene polyol compound may be 30 or less, 25 or less, 20 or less, 15 or less, 10 or less, 5 or less, or 4 or less. Accordingly, the sum (n+m) of n and m in Formula 1 above may be 3 or more, and may be also 30 or less, 25 or less, 20 or less, 15 or less, 10 or less, 5 or less, or 4 or less.

Contents about molecular weights of the core (A) in Formula 1, types of including polyethylene oxide and polypropylene oxide, and the like, as mentioned in this specification, may be contents about the core (A) in Formula 1 above itself or the polyalkylene polyol compound forming the core (A).

The weight average molecular weight of the core (A) in the compound of Formula 1 may be in a range of 1000 to 10,000. In the present application, the term weight average molecular weight is a converted value for standard polystyrene which is measured by GPC (Gel Permeation Chromatograph), and unless otherwise stated herein, the term molecular weight means a weight average molecular weight. In another example, the molecular weight of the core (A) may be 2,000 or more, 3,000 or more, 4,000 or more, 5,000 or more, or 6,000 or more. Also, in another example, the molecular weight of the core (A) may be about 9,000 or less, about 8,000 or less, about 7,000 or less, about 6,000 or less, or about 5,000 or less.

In the compound of Formula 1, the core (A) may contain at least one unit of a polyethylene oxide unit or a polypropylene oxide unit. When the core (A) contains both the above units, a ratio (P/E) of the number of moles of the polypropylene oxide unit (P) and the number of moles of the polyethylene oxide unit (E) in the core in the compound of Formula 1 may be in a range of 1 to 10. In another example, the ratio (P/E) may be 1.5 or more, 2 or more, 2.5 or more, 3 or more, 3.5 or more, or 4 or more. In another example, the ratio (P/E) may be 9.5 or less, 9 or less, 8.5 or less, 8 or less, 7.5 or less, 7 or less, 6.5 or less, 6 or less, 5.5 or less, or about 5 or less.

As the polyalkylene polyol compound capable of forming the core, for example, polyalkylene polyol compounds known as the names of KPX PP-2000, KPX PP-2600, KPX GP-4000, KPX-GP-5000, KPX GP-4000 or KPX-HP3753, and the like can be exemplified, but are not limited thereto.

In Formula 1, the core (A) and the chain (B) may each contain at least one polyalkylene oxide unit. Here, the specific form of the polyalkylene oxide unit is as described above.

Such a polyalkylene oxide unit can be represented, for example, by Formula A below.

  [Formula A]

In Formula A, L may be a linear or branched alkylene group having 2 to 12, 2 to 8 or 2 to 4 carbon atoms, or a linear or branched alkylene group having 2 or 3 carbon atoms.

For example, if L of Formula A is an alkyl group having 2 carbon atoms, Formula A above may be represented by Formula B and if it is an alkyl group having 3 carbon atoms, Formula A above may be represented by Formula C. Hereinafter, in this specification, the unit of Formula B below may be simply referred to as a PEG unit, and the unit of Formula C below may be simply referred to as a PPG unit.

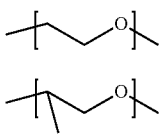

[Formula B]

[Formula C]

In one example, the core (A) and the chain (B) of Formula 1 may comprise a unit in which L in Formula A above has 2 or 3 carbon atoms, and may comprise, for example, a PEG or PPG unit.

The chain represented by K in Formula 1 may be represented by -L-R, and the chain represented by B may be represented by Formula 2 below. The left side of L in -L-R above and the left side of $L_1$ in Formula 2 below may be linked to the core (A).

The types of the linker (L) and the polymerizable functional group (R) in the chain represented by -L-R above are the same as those of Formula 2 to be described below.

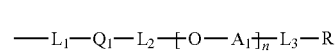  [Formula 2]

In Formula 2, $A_1$ is an alkylene group, $Q_1$ is an alicyclic or aromatic divalent residue, $L_1$ to $L_3$ are linkers, R is a polymerizable functional group or a residue of Formula 3 below, and n is any number.

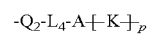  [Formula 3]

In Formula 3, $Q_2$ is an alicyclic or aromatic divalent residue, $L_4$ is a linker, A is a core part A in Formula 1, K is the same as K in Formula 1, p is a number of 2 or more, for example, a number in the range of about 2 to 4.

The alkylene group in Formula 2 may be, for example, a linear or branched alkylene group having 2 to 12 carbon atoms, 2 to 8 carbon atoms, or 2 to 4 carbon atoms. The alkylene group may optionally be substituted by one or more substituents.

The types of linkers of $L_1$ to $L_4$ in Formulas 2 and 3 and the linker (L) in -L-R- are not particularly limited and may be, for example, an oxygen atom, a sulfur atom, an alkylene group, an alkenylene group or an alkynylene group, or a linker represented by Formula D or E below. Here, the alkylene group may be a linear or branched alkylene group having 1 to 20 carbon atoms, 1 to 16 carbon atoms, 1 to 12 carbon atoms, 1 to 8 carbon atoms, or 1 to 4 carbon atoms, and the alkenylene group or alkynylene group may be a linear or branched alkenylene group or alkynylene group having 2 to 20 carbon atoms, 2 to 16 carbon atoms, 2 to 12 carbon atoms, 2 to 8 carbon atoms, or 2 to 4 carbon atoms.

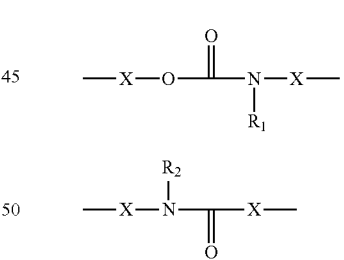

[Formula D]

[Formula E]

In Formulas D and E, each X is independently a single bond, an alkylene group, an oxyalkylene group or an alkyleneoxy group.

In addition, in Formulas D and E, $R_1$ and $R_2$ may be each independently a hydrogen atom or an alkyl group.

In Formulas 2 and 3, the alicyclic or aromatic divalent residue may be a divalent residue derived from an alicyclic compound or an aromatic compound.

In the above, the aromatic compound may mean a compound comprising one benzene ring structure, or a structure in which two or more benzene rings are linked together while sharing one or two carbon atoms or are linked by any linker, or a derivative thereof. The aromatic compound may be, for example, a compound having 6 to 30 carbon atoms, 6 to 25 carbon atoms, 6 to 21 carbon atoms, 6 to 18 carbon atoms, or 6 to 13 carbon atoms.

In the above, the alicyclic compound means a compound containing a cyclic hydrocarbon structure other than an aromatic cyclic structure. The alicyclic compound may be, for example, a compound having 3 to 30 carbon atoms, 3 to 25 carbon atoms, 3 to 21 carbon atoms, 3 to 18 carbon atoms, or 3 to 13 carbon atoms, unless otherwise specified.

The structure of $-L_1-Q_1-L_2-$ or the structure of $-L_3-Q_2-L_4-$ in Formulas 2 and 3 may be a structure derived from a diisocyanate compound. Here, as the specific example of the diisocyanate compound, tolylene diisocyanate, xylene diisocyanate, diphenylmethane diisocyanate, hexamethylene diisocyanate, isoboron diisocyanate, tetramethylxylene diisocyanate, or naphthalene diisocyanate, and the like can be exemplified, but is not limited thereto.

$[-O-A_1-]_n$, which is a repeating unit contained in Formula 2, may be a unit derived from polyalkylene diol, that is, polyalkylene glycol. The hydroxy groups on both sides of the polyalkylene glycol may react with the isocyanate groups of the diisocyanate to form a chain structure. As the polyalkylene glycol, polyalkylene glycols containing a linear or branched alkylene group having 2 to 12, 2 to 8, or 2 to 4 carbon atoms, or a linear or branched alkylene group having 2 or 3 carbon atoms can be exemplified. Such a polyalkylene glycol may have a molecular weight in the range of about 1000 to 10,000. In another example, the molecular weight may be 2,000 or more, 3,000 or more, 4,000 or more, 5,000 or more, or 6,000 or more. Also, in another example, the molecular weight of the core (A) may be about 9,000 or less, about 8,000 or less, about 7,000 or less, about 6,000 or less, or about 5,000 or less.

In addition, A in Formula 3 above may be a core derived from a polyalkylene polyol compound such as A in Formula 1, and the details of the compound are as mentioned in Formula 1.

The compound of Formula 1 may have a molecular weight in the range of about 5,000 to 100,000. In another example, the molecular weight may be 7,000 or more, 8,000 or more, 9,000 or more, 10,000 or more, 15,000 or more, or 20,000 or more. Also, in another example, the molecular weight of the compound may be about 90,000 or less, about 80,000 or less, about 70,000 or less, about 60,000 or less, about 50,000 or less, about 40,000 or less, or about 30,000 or less.

In one example, when the chain represented by B in Formula 1 is a chain in which R in Formula 2 above is a polymerizable functional group, in Formula 1, n may be 0 and m may be a number of 3 or more. In this case, m may be 30 or less, 25 or less, 20 or less, 15 or less, 10 or less, 5 or less, or 4 or less.

Furthermore, when the chain represented by B in Formula 1 is a case in which R in Formula 2 above is represented by Formula 3 above, in Formula 1, n may be 1 or more, or 2 or more, and m may be a number of 1 or more. In the above case, n may be 5 or less, 4 or less, 3 or less, or 2 or less, and m may be 5 or less, 4 or less, 3 or less, 2 or less, or 1, where p in Formula 3 may be 2 or more and 5 or less, 4 or less, or 3 or less.

The compound of Formula 1 can be prepared, for example, by using polyalkylene polyol, a diisocyanate compound and an acrylate compound containing an isocyanate group at the terminal.

For example, when the isocynate group of the acrylate compound containing the icocyanate group at the terminal and the terminal hydroxy group of polyalkylene glycol as polyalkylene polyol are subjected to urethane reaction and the isocyanate group of the diisocyanate compound at the other terminal is subjected to urethane reaction, a precursor of a material, in which one terminal is an isocyanate group and R in Formula 2 is a polymerizable functional group, is produced, and when such a precursor is reacted with a polyalkylene polyol compound having 3 or more terminal hydroxy groups, a compound, in which in Formula 1, n is 0 and m is 3 or more, may be produced.

Alternatively, when the hydroxy groups at both terminals of the polyalkylene glycol are reacted with the diisocyanate compound, a compound containing a polyalkylene oxide repeating unit in the chain and having both side diisocyanates is produced, and when the compound produced by reacting the both side diisocyanates with the hydroxy group of the polyalkylene polyol is again reacted with the acrylate compound containing the isocyanate group at the terminal, a compound, in which in Formula 1, n is 2 or more and m is 1 or more and in Formula 2, R is Formula 3, may be produced.

The present application also relates to a curable composition comprising the compound of Formula 1 above. In the present application, the term "curable composition" may mean a composition that can be cross-linked or cured.

Since the curable composition comprises the compound having the specific structure, a cured product having appropriate cohesiveness and adhesion can be formed without an excessive increase in elastic modulus when cured, while exhibiting suitably low viscosity before curing.

Such a curable composition can be used in a variety of optical applications, for example, a so-called OCR (Optically Clear Resin).

The ratio of the compound of Formula 1 in the curable composition is not particularly limited, but may be about 1 to 20% by weight based on 100% of the total weight of the resin and the oligomer component in the relevant curable composition. In another example, the ratio may be about 18% by weight or less, 16% by weight or less, 14% by weight or less, 12% by weight or less, 10% by weight or less, 8% by weight or less, or 6% by weight or less.

The curable composition may further comprise a variety of other components as long as it comprises the compound of Formula 1 as described above, where the kind of such a component is not particularly limited. Curable compositions referred to as so-called OCRs comprise components such as reactive oligomers, nonreactive oligomers and initiators, and the curable composition of the present application may also comprise such components.

In one example, the curable composition may comprise other curable oligomers, in addition to the compound of Formula 1. As the curable oligomer, a curable oligomer having at least one polymerizable functional group may be used, and for example, a curable oligomer having one or two of the polymerizable functional groups may be used. The kind of the specific curable oligomer is not particularly limited, and for example, a polyurethane oligomer having a polyalkylene oxide repeating unit and one or two polymerizable functional groups may be used as the curable oligomer known in the art. As such an oligomer, an oligomer having a weight average molecular weight of about 9,000 to 25,000 can be used. Such a curable oligomer may be used, for example, in a ratio of 100 to 500 parts by weight, relative to 100 parts by weight of the compound of Formula 1.

Also, in one example, the curable composition may further comprise a non-curable oligomer, that is, an oligomer having no polymerizable functional group. Such a non-curable oligomer is also variously known in the art, and such a known component can be appropriately selected and used.

The kind of the specific non-curable oligomer is not particularly limited, and for example, as the non-curable oligomer known in the art, a polyurethane oligomer having a polyalkylene oxide repeating unit and no polymerizable functional group can be used. As such an oligomer, an oligomer having a weight average molecular weight of about 9,000 to 25,000 can be used. Such a curable oligomer may be used in a ratio of, for example, about 1,000 to 2,500 parts by weight, relative to 100 parts by weight of the compound of Formula 1.

Also, the curable composition may further comprise, as a monomer for dilution, a (meth)acrylate monomer known in the art, and the like. Such a curable oligomer may be used, for example, in a ratio of 800 to 2,500 parts by weight, relative to 100 parts by weight of the compound of Formula 1.

The curable composition may further comprise, in addition to the compound, a radical initiator, for example, a photo-radical initiator. Such a photopolymerization initiator can be used without any particular limitation as long as it can initiate polymerization of a radical curable component, and for example, a known ultraviolet polymerization initiator, a visible light polymerization initiator and the like can be used. The ratio of the initiator is not particularly limited, and may be included to such an extent to induce a suitable cross-linking reaction.

Also, an exemplary curable composition may further comprise, in addition to the above-described components, a variety of known components, such as for example, plasticizers, fillers, colorants, antirust agents or antioxidants, for example, known components noted to be used in formation of so-called OCRs, and the like.

In one example, the reactive components contained in the curable composition, that is, the components having a polymerizable functional group may be a mono-functional component having one of the polymerizable functional groups other than the compound of Formula 1.

The present application also relates to a cured product. An exemplary cured product may be formed by curing in the curable composition described above.

The present application also relates to a use of the curable composition or the cured product. The curable composition or the cured product may be usefully used as a use for bonding various optical members of a display device. For example, the curable composition or the cured product can be used for bonding a display body and an optical functional material. Such a display body can be, for example, a display element such as an LCD (Liquid Crystal Display), an EL (Electroluminescence) display device, an EL light, an electronic paper or a plasma display, to which a polarizing plate is attached for glass. An example of the optically functional material may include a transparent plastic plate, such as an acrylic plate (for example, a hard coating or an antireflection coating may be also treated on one side or both sides), a PC (polycarbonate) plate, a PET (polyethylene terephthalate) plate, a PEN (polyethylene naphthalate) plate, for the purpose of improving visibility and preventing breakage of a display element from external impact, a tempered glass (for example, a scattering prevention film may be also attached), or a touch panel input sensor, and the like.

For example, the curable composition or the cured product can also be usefully used as a use for bonding a transparent substrate, on which a transparent electrode is formed, and a transparent plate in a capacitive touch panel. The material of such a transparent substrate may be, for example, PC, PMMA (polymethyl methacrylate), a composite of PC and PMMA, COC (cyclo-olefin copolymer) or COP (cyclo-olefin polymer). The material of the transparent plate may be, for example, glass, PC, PMMA, a composite of PC and PMMA, COC or COP.

The curable composition or the cured product can also be usefully used, for example, as a use for bonding a touch panel and a sheet or plate on the touch panel. Such a sheet may be, for example, an icon sheet, a protective sheet, a decorative sheet, etc., and the material of the sheet may be, for example, PET, PC, COC or COP, and the like. An example of the plate may include a decorative plate or a protective plate, and the like, and the material of the plate may be, for example, PET, glass, PC, PMMA, a composite of PC and PMMA, COC, or COP, and the like. The material of the touch panel bonding the plate may be, for example, glass, PET, PC, PMMA, a composite of PC and PMMA, COC or COP, and the like.

The curable composition or the cured product can also be usefully used, for example, as a use for directly bonding a touch panel and a display panel in a display device. FIG. 1 illustratively shows a display device comprising a display panel (101) and a touch panel (102), wherein the display panel (101) and the touch panel (102) are bonded by the curable composition or the cured product (103).

The curable composition or the cured product can also be usefully used, for example, as a use for filling a spaced space between an optically functional material and a display panel which are spaced apart from each other by a spacer, in a display device. FIG. 2 illustratively shows a display device in which the optically functional material is a touch panel. Referring to FIG. 2, the display device may comprise a display panel (201), a touch panel (202) and a spacer (203) that separates the display panel from the touch panel, and in this case, the device may have a structure that the curable composition or the cured product (204) fills a space where the display panel and the touch panel are separated, a so-called a space of air gap.

When the curable composition or the cured product is applied to the display device, the other components constituting the device and the constitution method of the device are not particularly limited, and as long as the curable composition or the cured product is used, any material or method known in the corresponding field can be adapted.

Effects of the Invention

The present application can provide a novel compound of a certain structure and a curable composition comprising such a novel compound and a use thereof. If the curable composition comprising the novel compound is used, the cohesiveness of the cured product can be increased without increasing viscosity of the composition before curing, the increase of the elastic modulus can be also minimized, and the ratio of a nonreactive oligomer can be also minimized with an effect of improving the interfacial adhesion. The curable composition can be applied to a variety of optical applications and can be usefully used, for example, for bonding various optical functional members in a display device, for example, for directly bonding a touch panel and a display panel.

BRIEF DESCRIPTION OF DRAWINGS

FIGS. 1 and 2 are schematic diagrams of an exemplary display device of the present application.

FIG. 3 is a schematic diagram of a display device related to the background art.

FIG. 4 is the IR spectrum of the compound prepared in Example.

MODE FOR INVENTION

Hereinafter, the present application will be described in more detail through Examples according to the present application, but the scope of the present application is not limited to Examples to be described below.

1. IR Spectrum Measurement Method

The measurement conditions of the IR spectrum applied in this specification are as follows. Upon measuring, the air condition was set as the base line.
   <Measurement Conditions>
   Measuring instrument: Agilent Cary 660 FTIR Spectrometer
   ATR: PIKE Technologies 025-2018 Miracle Znse perf crystal plate
   Measured wavelength: 400 to 4000 nm
   Measuring temperature: 25° C.

2. Evaluation of Molecular Weight

The weight average molecular weight (Mn) was measured using GPC under the following conditions, and the measurement results were converted into standard polystyrene of Agilent system for preparing the calibration curve.
   <Measurement Conditions>
   Measuring instrument: Agilent GPC (Agilent 1200 series, U.S.)
   Column: Two PL Mixed B connected
   Column temperature: 40° C.
   Eluent: THF (tetrahydrofuran)
   Flow rate: 1.0 mL/min
   Concentration: ~1 mg/mL (100 μL injection)

3. Measurement of Storage Elastic Modulus

After curing the curable compositions obtained in Examples and Comparative Examples and cutting the cured products into a size of 8 mm in diameter and 1 mm in thickness to prepare circular samples, the elastic modulus of the samples was measured using an ARES (Advanced Rheometrics Expansion System) by a frequency sweep mode at 25° C. and a frequency of 1 Hz.

4. Tensile Strength Measurement

The tensile strength was measured using a UTM (Zwick/Roell Z005) by ASTM D412 method while stretching a specimen having a thickness of 1 mm at a speed of 50 mm/min.

5. Peeling Force Measurement

After curing the curable compositions obtained in Examples and Comparative Examples and cutting the cured products to a size of 15 mm in width, 100 mm in length and 250 μm in thickness to prepare specimens, the peeling force of these specimens was measured using a TA-XT2plus [Tension] at 25° C. with a peeling angle of 180° and a peeling speed of 300 mm/min.

Specifically, in a polarizing plate comprising a TAC (triacetyl cellulose) film as a protective film, after applying the curable composition on the TAC film to a thickness of about 250 μm and covering the prepared PET film having a width of 15 mm and a length of about 100 mm (thickness: 100 μm) thereon, the curable composition was cured to measure the peeling force against the polarizing plate, while peeling the PET film.

EXAMPLE 1

Preparation of the Compound of Formula 1

A compound, in which in Formula 1 above, n is 0, m is 3, B is a chain of Formula 2 and the chain of Formula 2 is represented by Formula F below, was synthesized by the following method. PPG (polypropylene glycol) (weight average molecular weight: 6000) and a catalyst (dibutyltin dilaurate) were injected in a weight ratio of 78:0.002 (PPG: catalyst) into a reactor equipped with a heating device, a condenser and a thermometer for refluxing reflux nitrogen gas and facilitating temperature control, and the temperature was gradually increased and maintained to 55° C. Thereafter, AOI (2-isocyanatoethyl acrylate) was slowly added in drops for 30 minutes to be finally in a weight ratio (PPG: catalyst:AOI) of 78:0.002:1.8 and further stirred at the same temperature for 1 hour to synthesize a first compound. The reaction time was determined through an IR spectrum, and the reaction was carried out until the NCO peak identified at 2270 cm$^{-1}$ in the IR spectrum before reaction completely disappeared.

Subsequently, the first compound was added in drops to the reactor where IPDI (isophorone diisocyanate), MEHQ (4-methoxyphenol) and a catalyst (dibutyltin dilaurate) were present, in a weight ratio of 2.9:0.17:0.003 (IPDI:MEHQ: catalyst) at 50° C. for 30 minutes, and reacted by further stirring the mixture at the same temperature for 30 minutes. The reaction time and the input of the first compound were adjusted until the area of the NCO peak identified at 2270 cm$^{-1}$ in the IR spectrum decreased to 50%. Polypropylene triol (GP-4000, KPX, weight average molecular weight: 4000) was further added thereto and reacted with further stirring the mixture at 65° C. for 4 hours to prepare the desired compound. Here, the input of polypropylene triol and the reaction time were controlled to such an extent that the NCO peak at 2270 cm$^{-1}$ completely disappeared through the IR. The weight average molecular weight (Mw) of the desired compound thus synthesized was about 26,000.

[Formula F]

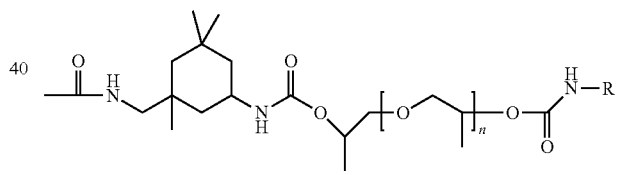

In Formula F, R is an acryloyloxyethyl group.

EXAMPLE 2

Curable Composition

The compound prepared in Example 1, a mono-functional reactive oligomer, a nonreactive oligomer, a monomer for dilution and an initiator were mixed in a weight ratio of 10:3:51:36:0.32 (reactive oligomer; compound of Example 1: nonreactive oligomer:monomer for dilution:initiator) to prepare a curable composition.

As the mono-functional reactive oligomer, a polyurethane oligomer derived from polypropylene glycol and having one acryloyloxy group and a molecular weight of about 17,000 was used, and as the nonreactive oligomer, a polyurethane oligomer derived from polypropylene glycol and having a molecular weight of about 17,000 was used, as the monomer for dilution, isobornyl acrylate was used, and as the initiator, a compound known as Irgacure 819 was used.

COMPARATIVE EXAMPLE 1

Preparation of Curable Composition

The mono-functional reactive oligomer and the nonreactive oligomer, the monomer for dilution, and the initiator, of Example 2 were mixed in a weight ratio of 10:54:36:0.32 (reactive oligomer:nonreactive oligomer:monomer for dilution:initiator) to prepare a curable composition.

COMPARATIVE EXAMPLE 2

Preparation of Curable Composition

The mono-functional reactive oligomer of Example 2, a bi-functional reactive oligomer, the nonreactive oligomer of Example 2, the monomer for dilution of Example 2, and the initiator of Example 2 were mixed in a weight ratio of 10:3:51:36:0.32 (reactive oligomer (mono-functional):reactive oligomer (bi-functional):nonreactive oligomer:monomer for dilution:initiator) to prepare a curable composition.

Here, as the bi-functional reactive oligomer, a polyurethane oligomer derived from polypropylene glycol and having two acryloyloxy groups and a molecular weight of about 17,000 was used.

COMPARATIVE EXAMPLE 3

Preparation of Curable Composition

The mono-functional reactive oligomer and the nonreactive oligomer, the monomer for dilution and the initiator, of Example 2, and MFA (DIPENTAERYTHRITOL HEXAACRYLATE) were mixed in a weight ratio of 10:51:36:0.32:3 (reactive oligomer:nonreactive oligomer:monomer for dilution:initiator:MFA) to prepare a curable composition.

The results of evaluating the measured physical properties of the curable compositions are summarized and described in Table 1 below.

TABLE 1

| | Storage Elastic Modulus | Viscosity | Tensile Strength | Adhesion |
|---|---|---|---|---|
| Example 2 | 23000 Pa | 3200 cps | 0.14 MPa | 700 gf/15 mm |
| C. Example 1 | 22000 Pa | 3300 cps | 0.04 MPa | 500 gf/15 mm |
| C. Example 2 | 28000 Pa | 4000 cps | 0.05 MPa | 350 gf/15 mm |
| C. Example 3 | 45000 Pa | 2000 cps | 0.10 MPa | 100 gf/15 mm |

(C. Example: Comparative Example)

From Table 1, it can be confirmed that the curable composition containing the specific compound of the present application exhibits proper cohesiveness, tensile strength and adhesion without excessively increasing the elastic modulus, if it is cured, while showing proper viscosity before curing.

The invention claimed is:

1. A compound represented by the Formula 1 below:

$$[K \!\!\!-\!\!\!\!\underset{n}{|}\!\!\!-\!\! A \!\!-\!\!\! B]_m \quad \text{[Formula 1]}$$

wherein, in the Formula 1,
A is a core comprising a polyalkylene oxide unit and derived from polyalkylene polyol,
B is a chain connected to said core, and is represented by Formula 2 below,
n is a number of 0 or more, m is a number of 1 or more, n+m is a number of 3 or more, and
K is -L-R, wherein said L is a linker and R is a polymerizable functional group that is an acryloyl group, an acryloyloxy group, a methacryloyl group or a methacryloyloxy group, $$-L_1-Q_1-L_2-(O-A_1)_n-L_3-R \quad \text{[Formula 2]}$$

wherein, in Formula 2, $A_1$ is an alkylene group, $Q_1$ is an alicyclic or aromatic divalent residue, $L_1$ to $L_3$ are each independently a linker, R is a polymerizable functional group or a residue of Formula 3 below, wherein the polymerizable functional group is an acryloyl group, an acryloyloxy group, a methacryloyl group or a methacryloyloxy group, and n is any number, $$-Q_2-L_4-A-(K)_p- \quad \text{[Formula 3]}$$

wherein, in Formula 3, $Q_2$ is an alicyclic or aromatic divalent residue, $L_4$ is a linker, A is the same as A in Formula 1, K is the same as K in Formula 1, and p is a number of 2 or more,
wherein $L_3$ in Formula 2 and L in the -L-R is represented by Formula D or E below:

[Formula D]
$$-X-O-\underset{R_1}{\overset{O}{\overset{\|}{C}}}-N-X-$$

[Formula E]
$$-X-\underset{}{\overset{R_2}{\overset{|}{N}}}-\overset{O}{\overset{\|}{C}}-X-$$

wherein, in Formulas D and E, each of X is independently a single bond, an alkylene group, an oxyalkylene group or an alkyleneoxy group, and $R_1$ and $R_2$ are each independently a hydrogen atom or an alkyl group.

2. The compound according to claim 1, wherein the polyalkylene oxide unit is a polyethylene oxide unit or a polypropylene oxide unit.

3. The compound according to claim 1, wherein the polyalkylene polyol has a weight average molecular weight in a range of 1000 to 10,000.

4. The compound according to claim 1, wherein $L_1$, $L_2$ and $L_4$ in Formulas 2 and 3 are each independently an oxygen atom, a sulfur atom, an alkylene group, an alkenylene group or an alkynylene group, or a linker represented by Formula D or E below:

[Formula D]
$$-X-O-\underset{R_1}{\overset{O}{\overset{\|}{C}}}-N-X-$$

-continued

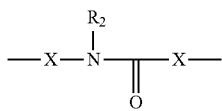
[Formula E]

wherein, in Formulas D and E, each of X is independently a single bond, an alkylene group, an oxyalkylene group or an alkyleneoxy group, and $R_1$ and $R_2$ are each independently a hydrogen atom or an alkyl group.

5. The compound according to claim 1, wherein the structure of $-L_1-Q_1-L_2-$ or the structure of $-L_3-Q_2-L_4-$ in Formulas 2 and 3 is a structure derived from a diisocyanate compound.

6. The compound according to claim 5, wherein the diisocyanate compound is tolylene diisocyanate, xylene diisocyanate, diphenylmethane diisocyanate, hexamethylene diisocyanate, isoboron diisocyanate, tetramethylxylene diisocyanate or naphthalene diisocyanate.

7. The compound according to claim 1, wherein $[O-A_1]_n$ in Formula 2 is a structure derived from polyalkylene glycol.

8. The compound according to claim 1, wherein in Formula 1, n is 0, m is a number of 3 or more, and in Formula 2:

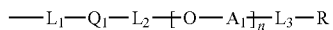

R is the polymerizable functional group.

9. The compound according to claim 1, wherein in Formula 1, n is 1 or more, m is 1 or more, and in Formula 2:

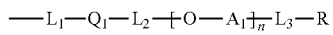

R is the residue of Formula 3

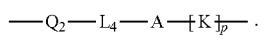

10. A curable composition comprising the compound of Formula 1 of claim 1.

11. A display panel comprising a display body and an optically functional material which are bonded with the curable composition of claim 10.

12. A display device comprising a touch panel and a display panel which are bonded with the curable composition of claim 10.

* * * * *